US010059780B2

(12) United States Patent
Yamaguchi et al.

(10) Patent No.: US 10,059,780 B2
(45) Date of Patent: Aug. 28, 2018

(54) METHOD FOR PRODUCING RUBBER PARTICLES WITH REDUCED COAGULATION TENDENCY, METHOD FOR PRODUCING PNEUMATIC TIRE, AND METHOD FOR PRODUCING RUBBER PRODUCT

(71) Applicants: SUMITOMO RUBBER INDUSTRIES, LTD., Kobe-shi, Hyogo (JP); TOHOKU UNIVERSITY, Sendai-shi, Miyagi (JP)

(72) Inventors: Haruhiko Yamaguchi, Kobe (JP); Yukino Inoue, Kobe (JP); Kazuhisa Fushihara, Kobe (JP); Seiji Takahashi, Sendai (JP); Satoshi Yamashita, Sendai (JP); Toru Nakayama, Sendai (JP)

(73) Assignee: SUMITOMO RUBBER INDUSTRIES, LTD., Kobe-Shi (JP)

( * ) Notice: Subject to any disclaimer, the term of this patent is extended or adjusted under 35 U.S.C. 154(b) by 182 days.

(21) Appl. No.: 15/170,278

(22) Filed: Jun. 1, 2016

(65) Prior Publication Data
US 2017/0002102 A1     Jan. 5, 2017

(30) Foreign Application Priority Data
Jun. 30, 2015 (JP) ................................. 2015-131025

(51) Int. Cl.
*C08C 19/22*     (2006.01)
*C07K 14/415*    (2006.01)

(52) U.S. Cl.
CPC ............ *C08C 19/22* (2013.01); *C07K 14/415* (2013.01)

(58) Field of Classification Search
CPC .............................. C08C 19/22; C07K 14/415
USPC ........................................................... 524/575
See application file for complete search history.

(56) References Cited

FOREIGN PATENT DOCUMENTS

| JP | 2000-316586 A |   | 11/2000 |            |
|----|---------------|---|---------|------------|
| JP | 2003310295 A  | * | 11/2003 |            |
| JP | 2005308412 A  | * | 11/2005 | G01N 33/543 |
| JP | 2011188776 A  | * | 9/2011  |            |

OTHER PUBLICATIONS

Berthelot et al., "Rubber Elongation Factor (REF), a Major Allergen Component in Hevea brasiliensis Latex Has Amyloid Properties," PLOS ONE, vol. 7, Issue 10, Oct. 25, 2012, e48065, pp. 1-12.
Berthelot et al., "Rubber particle proteins, HbREF and HbSRPP, show different interactions with model membranes," Biochimica et Biophysica Acta, vol. 1838, 2014 (Available online Sep. 12, 2013), pp. 287-299.

* cited by examiner

*Primary Examiner* — Kelechi C Egwim
(74) *Attorney, Agent, or Firm* — Birch, Stewart, Kolasch & Birch, LLP (57) ABSTRACT

Provided is a method for producing rubber particles with a reduced coagulation tendency. The present invention relates to a method for producing rubber particles with a reduced coagulation tendency, the method including a step of performing protein synthesis in the presence of both rubber particles and a cell-free protein synthesis solution containing an mRNA coding for a rubber elongation factor (REF) family protein to bind the REF family protein to the rubber particles.

7 Claims, 1 Drawing Sheet
Specification includes a Sequence Listing.

FIG.1

SEQUENCE LISTING

```
<160> NUMBER OF SEQ ID NOS: 12

<210> SEQ ID NO 1
<211> LENGTH: 27
<212> TYPE: DNA
<213> ORGANISM: Artificial Sequence
<220> FEATURE:
<223> OTHER INFORMATION: PRIMER-1

<400> SEQUENCE: 1
tttctcgaga tggctgaaga cgaagac                                    27
```

<210> SEQ ID NO 2
<211> LENGTH: 28
<212> TYPE: DNA
<213> ORGANISM: Artificial Sequence
<220> FEATURE:
<223> OTHER INFORMATION: PRIMER-2

<400> SEQUENCE: 2
tttggatcct caattctctc cataaaac                                           28

<210> SEQ ID NO 3
<211> LENGTH: 417
<212> TYPE: DNA
<213> ORGANISM: Hevea brasiliensis

<400> SEQUENCE: 3
atggctgaag acgaagacaa ccaacaaggg caggggagg ggttaaaata tttgggtttt         60
gtgcaagacg cggcaactta tgctgtgact accttctcaa acgtctatct ttttgccaaa       120
gacaaatctg gtccactgca gcctggtgtc gatatcattg agggtccggt gaagaacgtg       180
gctgtacctc tctataatag gttcagttat attcccaatg gagctctcaa gtttgtagac       240
agcacggttg ttgcatctgt cactattata gatcgctctc ttcccccaat tgtcaaggac       300
gcatctatcc aagttgtttc agcaattcga gctgccccag aagctgctcg ttctctggct       360
tcttctttgc ctgggcagac caagatactt gctaaggtgt tttatggaga gaattga         417

<210> SEQ ID NO 4
<211> LENGTH: 138
<212> TYPE: PRT
<213> ORGANISM: Hevea brasiliensis

<400> SEQUENCE: 4

Met Ala Glu Asp Glu Asp Asn Gln Gln Gly Gln Gly Glu Gly Leu Lys
1               5                   10                  15

Tyr Leu Gly Phe Val Gln Asp Ala Ala Thr Tyr Ala Val Thr Thr Phe
                20                  25                  30

Ser Asn Val Tyr Leu Phe Ala Lys Asp Lys Ser Gly Pro Leu Gln Pro
            35                  40                  45

Gly Val Asp Ile Ile Glu Gly Pro Val Lys Asn Val Ala Val Pro Leu
        50                  55                  60

Tyr Asn Arg Phe Ser Tyr Ile Pro Asn Gly Ala Leu Lys Phe Val Asp
65                  70                  75                  80

Ser Thr Val Val Ala Ser Val Thr Ile Ile Asp Arg Ser Leu Pro Pro
                85                  90                  95

Ile Val Lys Asp Ala Ser Ile Gln Val Val Ser Ala Ile Arg Ala Ala
            100                 105                 110

Pro Glu Ala Ala Arg Ser Leu Ala Ser Ser Leu Pro Gly Gln Thr Lys
        115                 120                 125

Ile Leu Ala Lys Val Phe Tyr Gly Glu Asn
    130                 135

<210> SEQ ID NO 5
<211> LENGTH: 31
<212> TYPE: DNA
<213> ORGANISM: Artificial Sequence
<220> FEATURE:
<223> OTHER INFORMATION: PRIMER-3

<400> SEQUENCE: 5
tttctcgaga tggatttgaa acctggagct g                                    31

<210> SEQ ID NO 6
<211> LENGTH: 33
<212> TYPE: DNA
<213> ORGANISM: Artificial Sequence
<220> FEATURE:
<223> OTHER INFORMATION: PRIMER-4

<400> SEQUENCE: 6
tttctcgagt catgtaccat aattttgctg cac                                  33

<210> SEQ ID NO 7
<211> LENGTH: 774
<212> TYPE: DNA
<213> ORGANISM: Hevea brasiliensis

<400> SEQUENCE: 7
atggatttga aacctggagc tggagggcag agagttaatc gattagtgga tccgattagt      60
tatcattttc ttcaatttct gtggcgtact ctacatcttc ttgtcagctt atggtacctt     120
caagttagta tggtccaaat gatcgaaggc tttctaatct ctagtggact tgtgaaacgc     180
tatggagccc tcgatattga caaggtccgg taccttgcca ttgtggtaga tagtgaagaa     240
gcttaccaaa tttctaaagt tattcagctt ttgaaatggg tggaagatat gggtgtgaaa     300
catttatgcc tctatgattc aaaaggagtt ctcaagacaa caagaaaac catcatggag      360
agtttgaaca atgctatgcc atttgaggaa gcagttgaaa agatgttttt actggaccag     420
aaacagatga ctgtggaatt tgcttccagc tccgatggaa ggaagcaat aaccagggca      480
gctaacgtac tctttatgaa gtatttgaag tatgctaaaa ctggtgtagg aaaggaagaa     540
ccatgcttta cagaagatca aatggatgag cactaaaag ctataggtta caagggccg      600
gaacctgact tgctattaat ttatggacct gttagatgcc atctaggttt ctcaccgtgg     660
agacttcgat atactgagat ggtgcatatg ggacccttga ggtacatgaa cctcggttca     720
ctaaaaaagg ccattcacag gttcacaaca gtgcagcaaa attatggtac atga          774

<210> SEQ ID NO 8
<211> LENGTH: 257
<212> TYPE: PRT
<213> ORGANISM: Hevea brasiliensis

<400> SEQUENCE: 8

Met Asp Leu Lys Pro Gly Ala Gly Gly Gln Arg Val Asn Arg Leu Val
1               5                   10                  15

Asp Pro Ile Ser Tyr His Phe Leu Gln Phe Leu Trp Arg Thr Leu His
            20                  25                  30

Leu Leu Val Ser Leu Trp Tyr Leu Gln Val Ser Met Val Gln Met Ile
        35                  40                  45

Glu Gly Phe Leu Ile Ser Ser Gly Leu Val Lys Arg Tyr Gly Ala Leu
    50                  55                  60

Asp Ile Asp Lys Val Arg Tyr Leu Ala Ile Val Val Asp Ser Glu Glu
65                  70                  75                  80

Ala Tyr Gln Ile Ser Lys Val Ile Gln Leu Leu Lys Trp Val Glu Asp
                85                  90                  95

Met Gly Val Lys His Leu Cys Leu Tyr Asp Ser Lys Gly Val Leu Lys
            100                 105                 110

Thr Asn Lys Lys Thr Ile Met Glu Ser Leu Asn Asn Ala Met Pro Phe
        115                 120                 125

Glu Glu Ala Val Glu Lys Asp Val Leu Leu Asp Gln Lys Gln Met Thr
            130                 135                 140

Val Glu Phe Ala Ser Ser Ser Asp Gly Lys Glu Ala Ile Thr Arg Ala
145                 150                 155                 160

Ala Asn Val Leu Phe Met Lys Tyr Leu Lys Tyr Ala Lys Thr Gly Val
                165                 170                 175

Gly Lys Glu Glu Pro Cys Phe Thr Glu Asp Gln Met Asp Glu Ala Leu
            180                 185                 190

Lys Ala Ile Gly Tyr Lys Gly Pro Glu Pro Asp Leu Leu Leu Ile Tyr
            195                 200                 205

Gly Pro Val Arg Cys His Leu Gly Phe Ser Pro Trp Arg Leu Arg Tyr
            210                 215                 220

Thr Glu Met Val His Met Gly Pro Leu Arg Tyr Met Asn Leu Gly Ser
225                 230                 235                 240

Leu Lys Lys Ala Ile His Arg Phe Thr Thr Val Gln Gln Asn Tyr Gly
                245                 250                 255

Thr

<210> SEQ ID NO 9
<211> LENGTH: 27
<212> TYPE: DNA
<213> ORGANISM: Artificial Sequence
<220> FEATURE:
<223> OTHER INFORMATION: PRIMER-5

<400> SEQUENCE: 9
tttctcgaga tggctgaaga ggtggag                                27

<210> SEQ ID NO 10
<211> LENGTH: 27
<212> TYPE: DNA
<213> ORGANISM: Artificial Sequence
<220> FEATURE:
<223> OTHER INFORMATION: PRIMER-6

<400> SEQUENCE: 10
tttggatcct tatgatgcct catctcc                                27

<210> SEQ ID NO 11
<211> LENGTH: 615
<212> TYPE: DNA
<213> ORGANISM: Hevea brasiliensis

<400> SEQUENCE: 11
atggctgaag aggtggagga agagaggcta aagtatttgg attttgtgcg agcggctgga        60
gtttatgctg tagattcttt ctcaactctc tacctttatg ccaaggacat atctggtcca       120
ttaaaacctg gtgtcgatac tattgagaat gtggtgaaga ccgtggttac tcctgtttat       180
tatattcccc ttgaggctgt caagtttgta gacaaaacgg tggatgtatc ggtcactagc       240
ctagatggcg ttgttccccc agttatcaag caggtgtctg cccaaactta ctcggtagct       300
caagatgctc caagaattgt tcttgatgtg gcttcttcag ttttcaacac tggtgtgcag       360
gaaggcgcaa aagctctgta cgctaatctt gaaccaaaag ctgagcaata tgcggtcatt       420
acctggcgtg ccctcaataa gctgccacta gttcctcaag tggcaaatgt agttgtgcca       480
accgctgttt atttctctga aaagtacaac gatgttgttc gtggcactac tgagcaggga       540
tatagagtgt cctcttattt gcctttgttg cccactgaga aaattactaa ggtgtttgga       600

```
gatgaggcat cataa                                            615
```

<210> SEQ ID NO 12
<211> LENGTH: 204
<212> TYPE: PRT
<213> ORGANISM: Hevea brasiliensis

<400> SEQUENCE: 12

```
Met Ala Glu Glu Val Glu Glu Arg Leu Lys Tyr Leu Asp Phe Val
1               5                   10                  15

Arg Ala Ala Gly Val Tyr Ala Val Asp Ser Phe Ser Thr Leu Tyr Leu
                20                  25                  30

Tyr Ala Lys Asp Ile Ser Gly Pro Leu Lys Pro Gly Val Asp Thr Ile
            35                  40                  45

Glu Asn Val Val Lys Thr Val Val Thr Pro Val Tyr Tyr Ile Pro Leu
    50                  55                  60

Glu Ala Val Lys Phe Val Asp Lys Thr Val Asp Val Ser Val Thr Ser
65                  70                  75                  80

Leu Asp Gly Val Val Pro Pro Val Ile Lys Gln Val Ser Ala Gln Thr
                85                  90                  95

Tyr Ser Val Ala Gln Asp Ala Pro Arg Ile Val Leu Asp Val Ala Ser
                100                 105                 110

Ser Val Phe Asn Thr Gly Val Gln Glu Gly Ala Lys Ala Leu Tyr Ala
            115                 120                 125

Asn Leu Glu Pro Lys Ala Glu Gln Tyr Ala Val Ile Thr Trp Arg Ala
    130                 135                 140

Leu Asn Lys Leu Pro Leu Pro Gln Val Ala Asn Val Val Val Pro
145                 150                 155                 160

Thr Ala Val Tyr Phe Ser Glu Lys Tyr Asn Asp Val Val Arg Gly Thr
                165                 170                 175

Thr Glu Gln Gly Tyr Arg Val Ser Ser Tyr Leu Pro Leu Leu Pro Thr
            180                 185                 190

Glu Lys Ile Thr Lys Val Phe Gly Asp Glu Ala Ser
    195                 200
```

METHOD FOR PRODUCING RUBBER PARTICLES WITH REDUCED COAGULATION TENDENCY, METHOD FOR PRODUCING PNEUMATIC TIRE, AND METHOD FOR PRODUCING RUBBER PRODUCT

TECHNICAL FIELD

The present invention relates to a method for producing rubber particles with a reduced coagulation tendency, a method for producing a pneumatic tire, and a method for producing a rubber product.

BACKGROUND ART

Rubber particles by nature tend to coagulate when left at room temperature. Hence, conventionally, rubber particles are kept at low temperatures to prevent coagulation during storage, transportation and other periods.

However, since enzymes involved in rubber synthesis are not activated at low temperatures, rubber cannot be efficiently synthesized from rubber particles at low temperatures. Accordingly, when natural rubber is synthesized from rubber particles in a test tube (or industrial plant), the temperature of the reaction solution needs to be raised to a temperature (approximately 37° C.) that activates the enzymes.

Rubber particles, which are harvested from the latex of rubber-producing plants, are particles coated with a lipid membrane. Since the membrane is a natural membrane, proteins that have been synthesized in the plants are bound to the surface of the membrane. Known examples of the proteins include rubber elongation factor (REF) and small rubber particle protein (SRPP) (see, for example, Non-Patent Literatures 1 and 2). It is also known that the decrease in the expression of the gene coding for REF in a rubber-producing plant results in a reduced ability to synthesize rubber.

Meanwhile, it is known that rubber synthesis is promoted when rubber particles are present with SRPP expressed in a recombinant microorganism engineered to express SRPP (see, for example, Patent Literature 1).

CITATION LIST

Patent Literature

Patent Literature 1: JP-A 2000-316586

Non-Patent Literature

Non-Patent Literature 1: Rubber particle proteins, HbREF and HbSRPP, show different interactions with model membranes, Biochimica et Biophysica Acta, 2014, volume 1838 (2014), pp. 287-299

Non-Patent Literature 2: Rubber Elongation Factor (REF), a major allergen component in *Hevea brasiliensis* latex has amyloid properties, PLOS ONE, 2012, volume 7, issue 10

SUMMARY OF INVENTION

Technical Problem

In view of the above problems associated with coagulation of rubber particles at room temperature, techniques are needed which can reduce coagulation of rubber particles even at temperatures that are not low, e.g. at room temperature.

The present invention aims to solve the above problems and to provide a method for producing rubber particles with a reduced coagulation tendency.

Solution to Problem

The present invention relates to a method for producing rubber particles with a reduced coagulation tendency, the method including a step of performing protein synthesis in the presence of both rubber particles and a cell-free protein synthesis solution containing an mRNA coding for a rubber elongation factor (REF) family protein to bind the REF family protein to the rubber particles.

The REF family protein is preferably derived from *Hevea brasiliensis*.

The cell-free protein synthesis solution preferably contains a germ extract.

The germ extract is preferably derived from wheat.

The rubber particles are preferably present in the cell-free protein synthesis solution at a concentration of 5 to 50 g/L.

The present invention also relates to a method for producing a pneumatic tire, the method including the steps of: synthesizing rubber from the rubber particles obtained by the method for producing rubber particles; kneading the rubber with an additive to obtain a kneaded mixture; building a green (or raw) tire from the kneaded mixture; and vulcanizing the green tire.

The present invention also relates to a method for producing a rubber product, the method including the steps of: synthesizing rubber from the rubber particles obtained by the method for producing rubber particles; kneading the rubber with an additive to obtain a kneaded mixture; forming a raw rubber product from the kneaded mixture; and vulcanizing the raw rubber product.

Advantageous Effects of Invention

The method for producing rubber particles with a reduced coagulation tendency of the present invention includes a step of performing protein synthesis in the presence of both rubber particles and a cell-free protein synthesis solution containing an mRNA coding for a rubber elongation factor (REF) family protein to bind the REF family protein to the rubber particles. With this method, by binding a REF family protein to rubber particles, the rubber particles are stabilized and exhibit a reduced coagulation tendency even at temperatures that are not low, e.g. at room temperature, and therefore rubber particles with a reduced coagulation tendency are produced. Accordingly, the rubber synthesis reaction can be continued while maintaining a large surface area (reaction area) of the rubber particles even at room temperature, and as a result, the rubber synthesis activity of the rubber particles is enhanced. Thus, it is possible to produce rubber more efficiently in reaction vessels (e.g. test tubes, industrial plants).

The method for producing a pneumatic tire of the present invention includes the steps of: synthesizing rubber from the rubber particles obtained by the method for producing rubber particles of the present invention; kneading the rubber with an additive to obtain a kneaded mixture; building a green tire from the kneaded mixture; and vulcanizing the green tire. With this method, a pneumatic tire is produced from rubber synthesized from rubber particles produced by a method that stabilizes rubber particles to reduce their coagulation. Thus, it is possible to use plant resources effectively to produce an environmentally friendly pneumatic tire.

The method for producing a rubber product of the present invention includes the steps of: synthesizing rubber from the rubber particles obtained by the method for producing rubber particles of the present invention; kneading the rubber with an additive to obtain a kneaded mixture; forming a raw rubber product from the kneaded mixture; and vulcanizing the raw rubber product. With this method, a rubber product is produced from rubber synthesized from rubber particles produced by a method that stabilizes rubber particles to reduce their coagulation. Thus, it is possible to use plant resources effectively to produce an environmentally friendly rubber product.

DESCRIPTION OF EMBODIMENTS

The method for producing rubber particles with a reduced coagulation tendency of the present invention includes a step of performing protein synthesis in the presence of both rubber particles and a cell-free protein synthesis solution containing an mRNA coding for a rubber elongation factor (REF) family protein to bind the REF family protein to the rubber particles. In other words, rubber particles bound to a REF family protein are obtained by performing protein synthesis in the presence of both rubber particles and a cell-free protein synthesis solution containing an mRNA coding for the REF family protein, or, more specifically, using a mixture of rubber particles with a cell-free protein synthesis solution containing an mRNA coding for the REF family protein.

Since liposomes are produced artificially as lipid bilayer membranes consisting of phospholipids, glyceroglycolipids, cholesterol and other components, the produced liposomes have no proteins bound to their surface. On the other hand, although rubber particles harvested from the latex of rubber-producing plants are also coated with a lipid membrane, the membrane of rubber particles is a naturally derived membrane in which proteins that have been synthesized in the plants are already bound to the surface of the membrane. Hence, binding of an additional protein to rubber particles that are already bound to and coated with proteins is expected to be more difficult than binding to liposomes not bound to any protein. There is also concern that the proteins already bound to rubber particles could inhibit cell-free protein synthesis.

For these reasons, difficulties have been anticipated in achieving cell-free protein synthesis in the presence of rubber particles. Under such circumstances, the present inventors performed cell-free synthesis of a REF family protein in the presence of rubber particles, which had never been attempted in the past, and they have first discovered that rubber particles bound to a REF family protein can be produced by performing cell-free protein synthesis in the presence of rubber particles. They have also found that the rubber particles produced as above are stable so that their coagulation is reduced even at room temperature due to the REF family protein bound thereto. Although the involvement of REF family proteins in rubber synthesis in rubber-producing plants has so far been suggested, the action of the proteins has not been clearly revealed. The present inventors have first discovered that REF family proteins not only contribute to the stabilization of rubber particles but reduce coagulation of the rubber particles as well.

Conventionally, rubber particles are dispersed by means of surfactants or the like; however, surfactants can act as inhibitors of enzymatic activities. In contrast, since the REF family protein to be bound to rubber particles inherently exists on rubber particles in rubber-producing plants, the protein does not seem to inhibit rubber synthesis activity. Accordingly, with the rubber particles produced according to the present invention, the rubber synthesis reaction can be continued while maintaining a large surface area (reaction area) of the rubber particles even at room temperature, and as a result, the rubber synthesis activity of the rubber particles is enhanced. Thus, it is possible to produce rubber more efficiently in reaction vessels (e.g. test tubes, industrial plants).

The production method of the present invention may include any other step as long as it involves the above step. Moreover, each step may be performed once or repeated multiple times.

The above protein synthesis in the presence of both rubber particles and a cell-free protein synthesis solution containing an mRNA coding for a REF family protein is namely the synthesis of a REF family protein by cell-free protein synthesis, and the synthesized REF family protein maintains biological functions (the native state). As the cell-free protein synthesis is performed in the presence of rubber particles, the synthesized REF family protein in the native state can be bound to the rubber particles.

Herein, binding of a REF family protein to rubber particles by protein synthesis in the presence of both the cell-free protein synthesis solution and the rubber particles means that, for example, all or part of the REF family protein synthesized by the protein synthesis is incorporated into the rubber particles, or inserted into the membrane structure of the rubber particles. It is not limited to these embodiments and also includes embodiments in which, for example, the protein is localized on the surface or inside of the rubber particles.

In the present invention, any amount of a REF family protein may be bound to rubber particles.

The origin of the rubber particles is not particularly limited. For example, the rubber particles may be derived from the latex of a rubber-producing plant such as *Hevea brasiliensis*, *Taraxacum kok-saghyz*, *Parthenium argentatum*, *Sonchus oleraceus*, or *Ficus elastica*.

The particle size of the rubber particles is also not particularly limited. Rubber particles of a specific particle size may be sorted out and used, or a mixture of rubber particles of different particle sizes may be used. When rubber particles of a specific particle size are sorted out and used, the rubber particles may be either small rubber particles (SRP) with a small particle size or large rubber particles (LRP) with a large particle size.

Commonly used methods may be employed for sorting out the rubber particles of a specific particle size, including, for example, a method involving centrifugation, preferably multistage centrifugation. A specific method includes centrifugation at 500-1500×g, centrifugation at 1700-2500×g, centrifugation at 7000-9000×g, centrifugation at 15000-25000×g, and centrifugation at 40000-60000×g, carried out in that order. The treatment time for each centrifugation treatment is preferably at least 20 minutes, more preferably at least 30 minutes, still more preferably at least 40 minutes, but preferably 120 minutes or less, more preferably 90 minutes or less. The treatment temperature for each centrifugation treatment is preferably 0° C. to 10° C., more preferably 2° C. to 8° C., particularly preferably 4° C.

The mRNA coding for a REF family protein serves as a translation template that can be translated to synthesize the REF family protein.

The origin of the mRNA coding for a REF family protein is not particularly limited. The mRNA is preferably derived from plants, more preferably at least one selected from the group consisting of plants of the genera *Hevea, Sonchus, Taraxacum*, and *Parthenium*. Among these, it is still more preferably derived from at least one species of plant selected from the group consisting of *Hevea brasiliensis, Sonchus oleraceus, Parthenium argentatum*, and *Taraxacum koksaghyz*, particularly preferably *Hevea brasiliensis*.

The plant is not particularly limited, and examples include *Hevea* species such as *Hevea brasiliensis; Sonchus* species such as *Sonchus oleraceus, Sonchus asper*, and *Sonchus brachyotus; Solidago* species such as *Solidago altissima, Solidago virgaurea* subsp. *asiatica, Solidago virgaurea* subsp. *leipcarpa, Solidago virgaurea* subsp. *leipcarpa* f. *paludosa, Solidago virgaurea* subsp. *gigantea*, and *Solidago gigantea* Ait. var. *leiophylla Fernald; Helianthus* species such as *Helianthus annus, Helianthus argophyllus, Helianthus atrorubens, Helianthus debilis, Helianthus decapetalus*, and *Helianthus giganteus; Taraxacum* species such as dandelion (*Taraxacum*), *Taraxacum venustum* H. Koidz, *Taraxacum hondoense* Nakai, *Taraxacum platycarpum* Dahlst, *Taraxacum japonicum, Taraxacum officinale* Weber, and *Taraxacum kok-saghyz; Ficus* species such as *Ficus carica, Ficus elastica, Ficus pumila* L., *Ficus erecta* Thumb., *Ficus ampelas* Burm. f., *Ficus benguetensis* Merr., *Ficus irisana* Elm., *Ficus microcarpa* L. f., *Ficus septica* Burm. f., and *Ficus benghalensis; Parthenium* species such as *Parthenium argentatum*, and *Parthenium hysterophorus, Ambrosia artemisiifolia*; and lettuce (*Lactuca sativa*).

The method for preparing the mRNA coding for a REF family protein is not particular limited as long as the prepared mRNA serves as a translation template that can be translated to synthesize the REF family protein. For example, the mRNA may be prepared by extracting total RNA from the latex of a rubber-producing plant by, for example, the hot phenol method, synthesizing cDNA from the total RNA, obtaining a DNA fragment of a gene coding for a REF family protein using primers prepared based on the nucleotide sequence data of the gene coding for a REF family protein, and performing an ordinary in vitro transcription of the DNA fragment.

As used herein, the rubber elongation factor (REF) family protein refers to REF or small rubber particle protein (SRPP), which are rubber particle-associated proteins that are bound to rubber particles in the latex of a rubber-producing plant (e.g. *Hevea brasiliensis*).

The REF family proteins are characterized by having an amino acid sequence contained in the REF superfamily domain (NCBI accession No. pfam05755).

Specific examples of the REF include the following [1]:

[1] a protein having the amino acid sequence of SEQ ID NO: 4.

It is known that proteins having one or more amino acid substitutions, deletions, insertions, or additions relative to the original amino acid sequence can have the inherent function. Thus, specific examples of the REF also include the following [2]:

[2] a rubber particle-associated protein having an amino acid sequence containing one or more amino acid substitutions, deletions, insertions, and/or additions relative to the amino acid sequence of SEQ ID NO: 4, and being bound to rubber particles in latex.

In order to preserve the function of the REF, it preferably has an amino acid sequence containing one or more, more preferably 1 to 28, still more preferably 1 to 21, furthermore preferably 1 to 14, particularly preferably 1 to 7, most preferably 1 to 3, yet most preferably one amino acid substitution, deletion, insertion and/or addition relative to the amino acid sequence of SEQ ID NO: 4.

Among other amino acid substitutions, conservative substitutions are preferred. Specific examples include substitutions within each of the following groups in the parentheses: (glycine, alanine), (valine, isoleucine, leucine), (aspartic acid, glutamic acid), (asparagine, glutamine), (serine, threonine), (lysine, arginine), (phenylalanine, tyrosine), and the like.

It is also known that proteins with amino acid sequences having high sequence identity with the original amino acid sequence can also have similar function. Thus, specific examples of the REF also include the following [3]:

[3] a rubber particle-associated protein having an amino acid sequence having at least 80% sequence identity with the amino acid sequence of SEQ ID NO: 4, and being bound to rubber particles in latex.

In order to preserve the function of the REF, the sequence identity with the amino acid sequence of SEQ ID NO: 4 is preferably at least 85%, more preferably at least 90%, still more preferably at least 95%, particularly preferably at least 98%, most preferably at least 99%.

Specific examples of the SRPP include the following [4]:

[1] a protein having the amino acid sequence of SEQ ID NO: 12.

It is known that proteins having one or more amino acid substitutions, deletions, insertions, or additions relative to the original amino acid sequence can have the inherent function. Thus, specific examples of the SRPP also include the following [5]:

[5] a rubber particle-associated protein having an amino acid sequence containing one or more amino acid substitutions, deletions, insertions, and/or additions relative to the amino acid sequence of SEQ ID NO: 12, and being bound to rubber particles in latex.

In order to preserve the function of the SRPP, it preferably has an amino acid sequence containing one or more, more preferably 1 to 41, still more preferably 1 to 31, further more preferably 1 to 20, particularly preferably 1 to 10, most preferably 1 to 4, yet most preferably two amino acid substitutions, deletions, insertions and/or additions relative to the amino acid sequence of SEQ ID NO: 12.

Among other amino acid substitutions, conservative substitutions are preferred. Specific examples include substitutions within each of the following groups in the parentheses: (glycine, alanine), (valine, isoleucine, leucine), (aspartic acid, glutamic acid), (asparagine, glutamine), (serine, threonine), (lysine, arginine), (phenylalanine, tyrosine), and the like.

It is also known that proteins with amino acid sequences having high sequence identity with the original amino acid sequence can also have similar function. Thus, specific examples of the SRPP also include the following [6]:

[6] a rubber particle-associated protein having an amino acid sequence having at least 80% sequence identity with the amino acid sequence of SEQ ID NO: 12, and being bound to rubber particles in latex.

In order to preserve the function of the SRPP, the sequence identity with the amino acid sequence of SEQ ID NO: 12 is preferably at least 85%, more preferably at least 90%, still more preferably at least 95%, particularly preferably at least 98%, most preferably at least 99%.

The sequence identity between amino acid sequences or nucleotide sequences may be determined using the algorithm BLAST [Pro. Natl. Acad. Sci. USA, 90, 5873 (1993)] developed by Karlin and Altschul or FASTA [Methods Enzymol., 183, 63 (1990)] (all the above documents are incorporated herein by reference).

Whether it is a REF family protein may be determined by conventional techniques, such as by identifying the amino acid sequence and then determining whether it has an amino acid sequence contained in the REF superfamily domain (NCBI accession No. pfam05755).

Specific examples of the gene coding for REF include the following [1] and [2]:

[1] a DNA having the nucleotide sequence of SEQ ID NO: 3; and

[2] a DNA that hybridizes under stringent conditions with a DNA having a nucleotide sequence complementary to the nucleotide sequence of SEQ ID NO: 3, and codes for a rubber particle-associated protein that is bound to rubber particles in latex.

As used herein, the term "hybridizing" means a process in which a DNA hybridizes with a DNA having a specific nucleotide sequence or a part of the DNA. Accordingly, the DNA having a specific nucleotide sequence or part of the DNA may have a nucleotide sequence long enough to be usable as a probe in Northern or Southern blot analysis or as an oligonucleotide primer in polymerase chain reaction (PCR) analysis. The DNA used as a probe may have a length of at least 100 bases, preferably at least 200 bases, more preferably at least 500 bases although it may be a DNA of at least 10 bases, preferably of at least 15 bases in length.

Techniques to perform DNA hybridization experiments are well known. The hybridization conditions under which experiments are carried out may be determined according to, for example, Molecular Cloning, 2nd ed. and 3rd ed. (2001), Methods for General and Molecular Bacteriology, ASM Press (1994), Immunology methods manual, Academic press (Molecular), and many other standard textbooks (all the above documents are incorporated herein by reference).

The stringent conditions may include, for example, an overnight incubation at 42° C. of a DNA-immobilized filter and a DNA probe in a solution containing 50% formamide, 5×SSC (750 mM sodium chloride, 75 mM sodium citrate), 50 mM sodium phosphate (pH 7.6), 5×Denhardt's solution, 10% dextran sulfate, and 20 µg/l denatured salmon sperm DNA, followed by washing the filter for example in a 0.2×SSC solution at approximately 65° C. Less stringent conditions may also be used. Changes in the stringency may be accomplished through the manipulation of formamide concentration (lower percentages of formamide result in lower stringency), salt concentrations or temperature. For example, low stringent conditions include an overnight incubation at 37° C. in a solution containing 6×SSCE (20×SSCE: 3 mol/l sodium chloride, 0.2 mol/l sodium dihydrogen phosphate, 0.02 mol/l EDTA, pH 7.4), 0.5% SDS, 30% formamide, and 100 µg/l denatured salmon sperm DNA, followed by washing in a 1×SSC solution containing 0.1% SDS at 50° C. In addition, to achieve even lower stringency, washes performed following hybridization may be done at higher salt concentrations (e.g. 5×SSC) in the above-mentioned low stringent conditions.

Variations in the above various conditions may be accomplished through the inclusion or substitution of blocking reagents used to suppress background in hybridization experiments. The inclusion of blocking reagents may require modification of the hybridization conditions for compatibility.

The DNA capable of hybridizing under such stringent conditions may have a nucleotide sequence having at least 80%, preferably at least 90%, more preferably at least 95%, still more preferably at least 98%, particularly preferably at least 99% sequence identity with the nucleotide sequence of SEQ ID NO: 3 as calculated using a program such as BLAST or FASTA with the above-mentioned parameters.

Whether the DNA that hybridizes under stringent conditions with the aforementioned DNA is a DNA coding for a REF family protein may be determined by conventional techniques, such as by translating the DNA into an amino acid sequence and then determining whether the amino acid sequence has an amino acid sequence contained in the REF superfamily domain (NCBI accession No. pfam05755).

Specific examples of the gene coding for SRPP include the following [3] and [4]:

[3] a DNA having the nucleotide sequence of SEQ ID NO: 11; and

[4] a DNA that hybridizes under stringent conditions with a DNA having a nucleotide sequence complementary to the nucleotide sequence of SEQ ID NO: 11, and codes for a rubber particle-associated protein that is bound to rubber particles in latex.

The term "hybridizing" is as described above. Also, the stringent conditions are as described above.

The DNA capable of hybridizing under such stringent conditions may have a nucleotide sequence having at least 80%, preferably at least 90%, more preferably at least 95%, still more preferably at least 98%, particularly preferably at least 99% sequence identity with the nucleotide sequence of SEQ ID NO: 11 as calculated using a program such as BLAST or FASTA with the above-mentioned parameters.

Whether the DNA that hybridizes under stringent conditions with the aforementioned DNA is a DNA coding for a REF family protein may be determined by conventional techniques, such as by translating the DNA into an amino acid sequence and then determining whether the amino acid sequence has an amino acid sequence contained in the REF superfamily domain (NCBI accession No. pfam05755).

Also, conventional techniques may be employed to identify the amino acid sequence or the nucleotide sequence of the protein. For example, total RNA is extracted from a growing plant, the mRNA is optionally purified, and a cDNA is synthesized by a reverse transcription reaction. Subsequently, degenerate primers are designed based on the amino acid sequence of a known protein corresponding to the target protein, a DNA fragment is partially amplified by RT-PCR, and the sequence is partially identified. Then, the RACE method or the like is performed to identify the full-length nucleotide sequence or amino acid sequence. The RACE method (rapid amplification of cDNA ends method) refers to a method in which, when the nucleotide sequence of a cDNA is partially known, PCR is performed based on the nucleotide sequence information of such a known region to clone an unknown region extending to the cDNA terminal, and is capable of cloning the full-length cDNA by PCR without preparing a cDNA library.

The degenerate primers may each preferably be prepared from a plant-derived sequence having a highly similar sequence part to the target protein.

If the nucleotide sequence coding for the protein is known, it is possible to identify the full-length nucleotide sequence or amino acid sequence by designing a primer containing an initiation codon and a primer containing a termination codon using the known nucleotide sequence followed by performing RT-PCR using a synthesized cDNA as a template.

The cell-free protein synthesis solution may contain an mRNA coding for any other protein as long as it contains the mRNA coding for a REF family protein.

The origin of the mRNA coding for any other protein is not particularly limited, but is preferably derived from any of the plants described above, more preferably at least one selected from the group consisting of plants of the genera *Hevea, Sonchus, Taraxacum,* and *Parthenium*. Among these, it is still more preferably derived from at least one species of plant selected from the group consisting of *Hevea brasiliensis, Sonchus oleraceus, Parthenium argentatum,* and *Taraxacum kok-saghyz*, particularly preferably *Hevea brasiliensis*.

The other protein may be any protein without any limitations, but for purposes of enhancing the rubber synthesis activity of the rubber particles, it is preferably a protein that inherently exists on rubber particles in rubber-producing plants. The protein that exists on rubber particles may be a protein that binds to a large part of the membrane surface of rubber particles, or a protein that is inserted into and bound to the membrane of rubber particles, or a protein that forms a complex with another protein bound to the membrane so as to be present on the membrane surface.

Examples of the protein that inherently exists on rubber particles in rubber-producing plants include cis-prenyltransferase (CPT), Nogo-B receptor (NgBR), β-1,3-glucanase, and Hevein.

The other protein is preferably a protein that inherently exists on rubber particles in rubber-producing plants and is involved in rubber synthesis, among others. When such a protein involved in rubber synthesis is bound to rubber particles, the rubber synthesis activity of the rubber particles is enhanced, and therefore rubber can be produced more efficiently in reaction vessels (e.g. test tubes, industrial plants).

Specifically, the other protein is preferably CPT and/or NgBR.

In the present invention, cell-free synthesis of a REF family protein is performed in the presence of rubber particles. This cell-free protein synthesis may be carried out by methods similar to conventional methods using the cell-free protein synthesis solution in the present invention. Commonly used cell-free protein synthesis techniques may be employed for the cell-free protein synthesis system, such as a rapid translation system RTS500 (Roche Diagnostics); and wheat germ extracts prepared in accordance with Proc. Natl. Acad. Sci. USA, 97:559-564 (2000), JP-A 2000-236896, JP-A 2002-125693 or JP-A 2002-204689, and cell-free protein synthesis systems using the wheat germ extracts (JP-A 2002-204689, Proc. Natl. Acad. Sci. USA, 99:14652-14657 (2002)). All the above documents are incorporated herein by reference. Systems using germ extracts are preferred among these. Thus, in another suitable embodiment of the present invention, the cell-free protein synthesis solution contains a germ extract.

The source of the germ extract is not particularly limited. From the standpoint of translation efficiency, it is preferred to use a plant-derived germ extract when a plant protein is synthesized by cell-free protein synthesis. It is particularly preferred to use a wheat-derived germ extract. Thus, in another suitable embodiment of the present invention, the germ extract is derived from wheat.

The method for preparing the germ extract is not particularly limited, and may be carried out conventionally, as described in, for example, JP-A 2005-218357, incorporated herein by reference.

The cell-free protein synthesis solution used in the present invention preferably further contains a cyclic nucleoside monophosphate derivative or a salt thereof (hereinafter, also referred to simply as "activity enhancer"). Protein synthesis activity can be further enhanced by the inclusion of the activity enhancer.

The cyclic nucleoside monophosphate derivative or salt thereof is not particularly limited as long as it can enhance cell-free protein synthesis activity, and examples include adenosine-3',5'-cyclic monophosphoric acid and its salts; adenosine-3',5'-cyclic monophosphorothioic acid (Sp-isomer) and its salts; adenosine-3',5'-cyclic monophosphorothioic acid (Rp-isomer) and its salts; guanosine-3',5'-cyclic monophosphoric acid and its salts; guanosine-3',5'-cyclic monophosphorothioic acid (Sp-isomer) and its salts; guanosine-3',5'-cyclic monophosphorothioic acid (Rp-isomer) and its salts; 8-bromoadenosine-3',5'-cyclic monophosphoric acid (bromo-cAMP) and its salts; 8-(4-chlorophenylthio)adenosine-3',5'-cyclic monophosphoric acid (chlorophenylthio-cAMP) and its salts; 5,6-dichloro-1-β-D-ribofuranosylbenzimidazole adenosine-3',5'-cyclic monophosphoric acid (dichlororibofuranosylbenzimidazole cAMP) and its salts; adenosine-2',5'-cyclic monophosphoric acid and its salts; adenosine-2',5'-cyclic monophosphorothioic acid (Sp-isomer) and its salts; adenosine-2',5'-cyclic monophosphorothioic acid (Rp-isomer) and its salts; guanosine-2',5'-cyclic monophosphoric acid and its salts; guanosine-2',5'-cyclic monophosphorothioic acid (Sp-isomer) and its salts; and guanosine-2',5'-cyclic monophosphorothioic acid (Rp-isomer) and its salts.

The base that forms a salt with the cyclic nucleoside monophosphate derivative is not particularly limited as long as it is biochemically acceptable and forms a salt with the derivative. Preferred are, for example, alkali metal atoms such as sodium or potassium, and organic bases such as Tris-hydroxyaminomethane, among others.

Of these activity enhancers, adenosine-3',5'-cyclic monophosphoric acid or adenosine-3',5'-cyclic monophosphate sodium is particularly preferred. These activity enhancers may be used alone or in combinations of two or more.

The activity enhancer may be incorporated into the cell-free protein synthesis solution in the present invention in advance. If the activity enhancer is unstable in the solution, it is preferably added during the protein synthesis reaction performed in the presence of both the cell-free protein synthesis solution and rubber particles.

The amount of the activity enhancer added is not particularly limited as long as the activity enhancer is at a concentration that can activate (increase) the protein synthesis reaction in the cell-free protein synthesis solution in the present invention. Specifically, the final concentration in the reaction system may usually be at least 0.1 millimoles/liter. The lower limit of the concentration is preferably 0.2 millimoles/liter, more preferably 0.4 millimoles/liter, particularly preferably 0.8 millimoles/liter, while the upper limit of the concentration is preferably 24 millimoles/liter, more preferably 6.4 millimoles/liter, particularly preferably 3.2 millimoles/liter.

When adding the activity enhancer to the cell-free protein synthesis solution in the present invention, the temperature of the cell-free protein synthesis solution is not particularly limited, but is preferably 0° C. to 30° C., more preferably 10° C. to 26° C.

In addition to the mRNA (translation template) coding for a REF family protein, the cell-free protein synthesis solution in the present invention also contains ATP, GTP, creatine phosphate, creatine kinase, L-amino acids, potassium ions, magnesium ions and other components required for protein synthesis, and optionally an activity enhancer. Such a cell-free protein synthesis solution can serve as a cell-free protein synthesis reaction system.

Since the germ extract prepared by the method described in JP-A 2005-218357 contains tRNA in an amount necessary for protein synthesis reaction, addition of separately prepared tRNA is not required when the germ extract prepared by the above method is used in the cell-free protein synthesis solution. In other words, tRNA may be added to the cell-free protein synthesis solution as necessary.

In the present invention, protein synthesis is performed in the presence of both rubber particles and a cell-free protein synthesis solution containing an mRNA coding for a REF family protein. Specifically, this can be accomplished by adding rubber particles to the cell-free protein synthesis solution at a suitable point either before or after protein synthesis, preferably before protein synthesis.

The rubber particles are preferably present in the cell-free protein synthesis solution at a concentration of 5 to 50 g/L. In other words, 5 to 50 g of rubber particles are preferably present in 1 L of the cell-free protein synthesis solution. When the concentration of rubber particles present in the cell-free protein synthesis solution is less than 5 g/L, a rubber layer may not be formed by separation treatment (e.g. ultracentrifugation) for collecting the rubber particles bound to the synthesized REF family protein, and therefore it may be difficult to collect the rubber particles bound to the synthesized REF family protein. When the concentration of rubber particles present in the cell-free protein synthesis solution exceeds 50 g/L, the rubber particles may coagulate, so that the synthesized REF family protein may fail to bind well to the rubber particles. The concentration of rubber particles is more preferably 10 to 40 g/L, still more preferably 15 to 35 g/L, particularly preferably 15 to 30 g/L.

In the protein synthesis in the presence of both rubber particles and the cell-free protein synthesis solution, rubber particles may be added as appropriate as the reaction progresses. The cell-free protein synthesis solution and rubber particles are preferably present together during the period when the cell-free protein synthesis system is active, such as 3 to 48 hours, preferably 3 to 30 hours, more preferably 3 to 24 hours after the addition of rubber particles to the cell-free protein synthesis solution.

The rubber particles do not have to be subjected to any treatment, e.g. pretreatment, before being combined with the cell-free protein synthesis solution. However, proteins may be removed from the rubber particles with a surfactant beforehand to increase the proportion of the REF family protein desired to be bound by the method of the present invention, among the proteins present on the rubber particles. Thus, in another suitable embodiment of the present invention, the rubber particles used in the present invention are washed with a surfactant before being combined with the cell-free protein synthesis solution.

The surfactant is not particularly limited, and examples include nonionic surfactants and amphoteric surfactants. Nonionic surfactants and amphoteric surfactants, among others, are suitable because they have only a little denaturing effect on the proteins on the membrane, and amphoteric surfactants are especially suitable. Thus, in another suitable embodiment of the present invention, the surfactant is an amphoteric surfactant.

These surfactants may be used alone or in combinations of two or more.

Examples of nonionic surfactants include polyoxyalkylene ether nonionic surfactants, polyoxyalkylene ester nonionic surfactants, polyvalent alcohol fatty acid ester nonionic surfactants, sugar fatty acid ester nonionic surfactants, alkyl polyglycoside nonionic surfactants, and polyoxyalkylene polyglucoside nonionic surfactants; and polyoxyalkylene alkylamines and alkyl alkanolamides.

Of these, polyoxyalkylene ether nonionic surfactants or polyvalent alcohol fatty acid ester nonionic surfactants are preferred.

Examples of polyoxyalkylene ether nonionic surfactants include polyoxyalkylene alkyl ethers, polyoxyalkylene alkylphenyl ethers, polyoxyalkylene polyol alkyl ethers, and polyoxyalkylene mono-, di- or tristyryl phenyl ethers. Among these, polyoxyalkylene alkylphenyl ethers are suitable. The polyol is preferably a $C_{2-12}$ polyvalent alcohol, such as ethylene glycol, propylene glycol, glycerin, sorbitol, glucose, sucrose, pentaerythritol, or sorbitan.

Examples of polyoxyalkylene ester nonionic surfactants include polyoxyalkylene fatty acid esters and polyoxyalkylene alkyl rosin acid esters.

Examples of polyvalent alcohol fatty acid ester nonionic surfactants include fatty acid esters of $C_{2-12}$ polyvalent alcohols and fatty acid esters of polyoxyalkylene polyvalent alcohols. More specific examples include sorbitol fatty acid esters, sorbitan fatty acid esters, glycerin fatty acid esters, polyglycerin fatty acid esters, and pentaerythritol fatty acid esters, as well as polyalkylene oxide adducts of the foregoing (e.g. polyoxyalkylene sorbitan fatty acid esters, polyoxyalkylene glycerin fatty acid esters). Among these, sorbitan fatty acid esters are suitable.

Examples of sugar fatty acid ester nonionic surfactants include fatty acid esters of sucrose, glucose, maltose, fructose and polysaccharides, as well as polyalkylene oxide adducts of the foregoing.

Examples of alkyl polyglycoside nonionic surfactants include those having glucose, maltose, fructose, sucrose and the like as glycosides, such as alkyl glucosides, alkyl polyglucosides, polyoxyalkylene alkyl glucosides, and polyoxyalkylene alkyl polyglucosides, as well as fatty acid esters of the foregoing. Polyalkylene oxide adducts of any of the foregoing may also be used.

Examples of the alkyl groups in these nonionic surfactants include $C_{4-30}$ linear or branched, saturated or unsaturated alkyl groups. The polyoxyalkylene groups may have $C_{2-4}$ alkylene groups, and may have about 1-50 moles of added ethylene oxide, for example. Examples of the fatty acids include $C_{4-30}$ linear or branched, saturated or unsaturated fatty acids.

Of the nonionic surfactants, polyoxyethylene (10) octylphenyl ether (Triton X-100) or sorbitan monolaurate (Span 20) is particularly preferred for their ability to moderately remove membrane-bound proteins while keeping the membrane of rubber particle stable and, further, having only a little denaturing effect on the proteins.

Examples of amphoteric surfactants include zwitterionic surfactants such as quaternary ammonium group/sulfonate group ($—SO_3H$) surfactants, water-soluble quaternary ammonium group/phosphate group surfactants, water-insoluble quaternary ammonium group/phosphate group surfactants, and quaternary ammonium group/carboxyl group surfactants. The acid groups in these zwitterionic surfactants may be salts.

In particular, the zwitterionic surfactant preferably has both positive and negative charges in a molecule, and the acid dissociation constant (pKa) of the acid group is preferably 5 or less, more preferably 4 or less, still more preferably 3 or less.

Specific examples of the amphoteric surfactant include ammonium sulfobetaines such as 3-[3-cholamidopropyl) dimethylamino]-2-hydroxy-1-propanesulfonate (CHAPSO), 3-[3-cholamidopropyl)dimethylamino]-propanesulfonate (CHAPS), N,N-bis(3-D-gluconamidopropyl)-cholamide, n-octadecyl-N,N'-dimethyl-3-amino-1-propanesulfonate, n-decyl-N,N'-dimethyl-3-amino-1-propanesulfonate, n-dodecyl-N,N'-dimethyl-3-amino-1-propanesulfonate, n-tetradecyl-N,N'-dimethyl-3-amino-1-propanesulfonate (Zwittergent™-3-14}, n-hexadecyl-N,N'-dimethyl-3-amino-1-propanesulfonate, and n-octadecyl-N,N'-dimethyl-3-amino-1-propanesulfonate; phosphocholines such as n-octylphosphocholine, n-nonylphosphocholine, n-decylphosphocholine, n-dodecylphosphocholine, n-tetradecylphosphocholine, and n-hexadecylphosphocholine; and phosphatidylcholines such as dilauroyl phosphatidylcholine, dimyristoyl phosphatidylcholine, dipalmitoyl phosphatidylcholine, distearoyl phosphatidylcholine, dioleoyl phosphatidylcholine, and dilinoleoyl phosphatidylcholine. Of these, 3-[(3-cholamidopropyl)dimethylamino]-propanesulfonate (CHAPS) is particularly preferred for its ability to moderately remove proteins while keeping the membrane of rubber particles stable.

The concentration of the surfactant for the treatment is preferably within three times the critical micelle concentration (CMC) of the surfactant used. The membrane stability of the rubber particles may be reduced if they are treated with the surfactant at a concentration exceeding three times the critical micelle concentration. The concentration is more preferably within 2.5 times, still more preferably within 2.0 times the CMC. The lower limit of the concentration is preferably 0.05 times or more, more preferably 0.1 times or more, still more preferably 0.3 times or more the CMC.

Examples of reaction systems or apparatuses that can be used in the protein synthesis in the present invention include a batch method (Pratt, J. M. et al., Transcription and Translation, Hames, 179-209, B. D. & Higgins, S. J., eds, IRL Press, Oxford (1984)), a continuous cell-free protein synthesis system in which amino acids, energy sources and the like are supplied continuously to the reaction system (Spirin, A. S. et al., Science, 242, 1162-1164 (1988)), a dialysis method (Kigawa et al., 21st Annual Meeting of the Molecular Biology Society of Japan, WID 6) and an overlay method (instruction manual of PROTEIOS™ Wheat germ cell-free protein synthesis core kit, Toyobo Co., Ltd.). All the above documents are incorporated herein by reference. Another method may be to supply template RNA, amino acids, energy sources and the like as necessary to the protein synthesis reaction system, and discharge the synthesis product or decomposition product as required.

Among these, the overlay method has the advantage of easy operation, but unfortunately the rubber particles disperse in the reaction solution and thus are difficult to efficiently bind to the synthesized REF family protein, while, in the dialysis method, since the amino acids used as raw materials of the REF family protein to be synthesized can pass through the dialysis membrane but the rubber particles cannot pass therethrough, the dispersal of the rubber particles can be prevented, and thus it is possible to efficiently bind the synthesized REF family protein to the rubber particles. Accordingly, the dialysis method is preferred.

The dialysis method refers to a method in which protein synthesis is carried out using the protein synthesis reaction solution in the present invention as an inner dialysis solution, and an apparatus in which the inner dialysis solution is separated from an outer dialysis solution by a dialysis membrane capable of mass transfer. Specifically, for example, a translation template is added to the synthesis reaction solution excluding the translation template, optionally after pre-incubation for an appropriate amount of time, and then the solution is put in a suitable dialysis container as the inner reaction solution. Examples of the dialysis container include containers with a dialysis membrane attached to the bottom (e.g. Dialysis Cup 12000 available from Daiichi Kagaku) and dialysis tubes (e.g. 12000 available from Sanko Junyaku Co., Ltd.). The dialysis membrane used has a molecular weight cutoff of 10,000 daltons or more, preferably about 12,000 daltons.

The outer dialysis solution used is a buffer containing amino acids. The dialysis efficiency can be increased by replacing the outer dialysis solution with a fresh solution when the reaction speed declines. The reaction temperature and time are selected appropriately according to the protein synthesis system used. For example, in the case of a system using a wheat-derived germ extract, the reaction may be carried out usually at 10° C. to 40° C., preferably 18° C. to 30° C., more preferably 20° C. to 26° C., for 10 minutes to 48 hours, preferably for 10 minutes to 30 hours, more preferably for 10 minutes to 24 hours.

Since the mRNA coding for a REF family protein contained in the cell-free protein synthesis solution in the present invention is easily broken down, the mRNA may be additionally added as appropriate during the protein synthesis reaction to make the protein synthesis more efficient. Thus, in another suitable embodiment of the present invention, the mRNA coding for a REF family protein is additionally added during the protein synthesis reaction.

The addition time, the number of additions, the addition amount and other conditions of the mRNA are not particularly limited, and may be selected appropriately.

In the production method of the present invention, a step of collecting the rubber particles may optionally be performed after the step of performing protein synthesis in the presence of both rubber particles and a cell-free protein synthesis solution containing an mRNA coding for a REF family protein to bind the REF family protein to the rubber particles.

The rubber particle collection step may be carried out by any method, provided that the rubber particles can be collected. It may be carried out by conventional methods for collecting rubber particles. Specific examples include methods using centrifugation. When the rubber particles are collected by the centrifugation, the centrifugal force, centrifugation time and centrifugation temperature may be selected appropriately so as to allow the rubber particles to be collected. For example, the centrifugal force during the centrifugation is preferably 15000×g or more, more preferably 20000×g or more, still more preferably 25000×g or more. Since increasing the centrifugal force too much is not expected to produce a correspondingly high separation effect, the upper limit of the centrifugal force is preferably 50000×g or less, more preferably 45000×g or less. The centrifugation time is preferably at least 20 minutes, more preferably at least 30 minutes, still more preferably at least 40 minutes. Since increasing the centrifugation time too much is not expected to produce a correspondingly high separation effect, the upper limit of the centrifugation time is preferably 120 minutes or less, more preferably 90 minutes or less.

From the standpoint of maintaining the protein activity of the REF family protein bound to the rubber particles, the centrifugation temperature is preferably 0° C. to 10° C., more preferably 2° C. to 8° C., particularly preferably 4° C.

The rubber particles and the cell-free protein synthesis solution are separated into the upper layer and the lower layer, respectively, by the centrifugation. The cell-free protein synthesis solution as the lower layer may then be removed to collect the rubber particles bound to the REF family protein. The collected rubber particles may be re-suspended in a suitable buffer with a neutral pH for storage.

Since the REF family protein to be bound to the rubber particles is a protein that inherently exists on rubber particles in rubber-producing plants, the rubber particles collected by the rubber particle collection step can be used in the same way as usual natural rubber without the need for further special treatment.

As described above, according to the present invention, a REF family protein can be bound to rubber particles by performing protein synthesis in the presence of both the rubber particles and a cell-free protein synthesis solution containing an mRNA coding for the REF family protein. By binding a REF family protein to rubber particles as described above, the rubber particles are stabilized and exhibit a reduced coagulation tendency even at temperatures that are not low, e.g. at room temperature, and therefore rubber particles with a reduced coagulation tendency are produced. Thus, another aspect of the present invention is a method for reducing coagulation of rubber particles, which includes a step of performing protein synthesis in the presence of both rubber particles and a cell-free protein synthesis solution containing an mRNA coding for a REF family protein to bind the REF family protein to the rubber particles.

The step of performing protein synthesis in the presence of both rubber particles and a cell-free protein synthesis solution containing an mRNA coding for a REF family protein to bind the REF family protein to the rubber particles is as described above.

(Method for Producing Rubber Product)

The method for producing a rubber product of the present invention includes the steps of: synthesizing rubber from the rubber particles obtained by the method for producing rubber particles; kneading the rubber with an additive to obtain a kneaded mixture; forming a raw rubber product from the kneaded mixture; and vulcanizing the raw rubber product.

The rubber product is not particularly limited as long as it is a rubber product that can be produced from rubber, preferably natural rubber, and examples include pneumatic tires, rubber rollers, rubber fenders, gloves, and medical rubber tubes.

When the rubber product is a pneumatic tire, or in other words when the method for producing a rubber product of the present invention is a method for producing a pneumatic tire, the raw rubber product forming step corresponds to a green tire building step in which a green tire is built from the kneaded mixture, and the vulcanization step corresponds to a vulcanization step in which the green tire is vulcanized. Thus, the method for producing a pneumatic tire of the present invention includes the steps of: synthesizing rubber from the rubber particles obtained by the method for producing rubber particles; kneading the rubber with an additive to obtain a kneaded mixture; building a green (or raw) tire from the kneaded mixture; and vulcanizing the green tire.

<Synthesis Step>

In the synthesis step, rubber is synthesized from the rubber particles obtainable by the method for producing rubber particles. The synthesis of rubber from the rubber particles may be carried out by conventional methods, for example, by mixing the rubber particles with substrates used as raw materials of rubber in a reaction vessel (e.g. a test tube or industrial plant).

<Kneading Step>

In the kneading step, the rubber obtained by the synthesis step is kneaded with an additive to obtain a kneaded mixture.

The rubber obtained by the synthesis step is one obtained by subjecting the synthesized rubber particles to the following solidification step.

<Solidification Step>

The synthesized rubber particles are subjected to a solidification step. The method for solidification is not particularly limited, and examples include a method of adding the rubber particles to a solvent that does not dissolve the polyisoprenoid (natural rubber), such as ethanol, methanol or acetone; and a method of adding an acid to the rubber particles. Rubber (natural rubber) can be recovered as solids from the rubber particles by the solidification step. The obtained rubber (natural rubber) may be dried as necessary before use.

The additive is not particularly limited, and additives used in production of rubber products may be used. For example, when the rubber product is a pneumatic tire, examples include rubber components other than the rubber synthesized from the rubber particles, reinforcing fillers such as carbon black, silica, calcium carbonate, alumina, clay, or talc, silane coupling agents, zinc oxide, stearic acid, processing aids, various antioxidants, softeners such as oil, wax, vulcanizing agents such as sulfur, and vulcanization accelerators.

The kneading in the kneading step may be carried out using an open roll mill, a Banbury mixer, an internal mixer, or other rubber kneading machines.

<Raw Rubber Product Forming Step (Green Tire Building Step for Tire)>

In the raw rubber product forming step, a raw rubber product (green tire for tire) is formed (or built) from the kneaded mixture obtained in the kneading step.

The method for forming a raw rubber product is not particularly limited, and methods used to form raw rubber products may be used appropriately. For example, when the rubber product is a pneumatic tire, the kneaded mixture obtained in the kneading step may be extruded according to the shape of a tire component and then formed by a usual method on a tire building machine and assembled with other tire components to build a green tire (unvulcanized tire).

<Vulcanization Step>

In the vulcanization step, the raw rubber product obtained in the raw rubber product forming step is vulcanized to obtain a rubber product.

The method for vulcanizing the raw rubber product is not particularly limited, and methods used to vulcanize raw rubber products may be used appropriately. For example, when the rubber product is a pneumatic tire, the green tire (unvulcanized tire) obtained in the green tire building step may be vulcanized by heating and pressing in a vulcanizer to obtain a pneumatic tire.

EXAMPLES

The present invention is specifically described with reference to examples, but the present invention is not limited to these examples.

Example 1

Extraction of Total RNA from *Hevea* Latex

Total RNA was extracted from the latex of *Hevea brasiliensis* by the hot phenol method. To 6 mL of the latex were added 6 mL of 100 mM sodium acetate buffer and 1 mL of a 10% SDS solution, and then 12 mL of water-saturated phenol pre-heated at 65° C. The mixture was incubated for 5 minutes at 65° C., agitated in a vortex, and centrifuged at 7000 rpm for 10 minutes at room temperature. After the centrifugation, the supernatant was transferred to a new tube, 12 mL of a phenol:chloroform (1:1) solution was added, and the mixture was agitated by shaking for 2 minutes. After the agitation, the resulting mixture was centrifuged again at 7000 rpm for 10 minutes at room temperature, the supernatant was transferred to a new tube, 12 mL of a chloroform:isoamyl alcohol (24:1) solution was added, and the mixture was agitated by shaking for 2 minutes. After the agitation, the resulting mixture was centrifuged again at 7000 rpm for 10 minutes at room temperature, the supernatant was transferred to a new tube, 1.2 mL of a 3M sodium acetate solution and 13 mL of isopropanol were added, and the mixture was agitated in a vortex. The resulting mixture was incubated for 30 minutes at −20° C. to precipitate total RNA.

The incubated mixture was centrifuged at 15000 rpm for 10 minutes at 4° C., and the supernatant was removed to collect a precipitate of total RNA. The collected total RNA was washed twice with 70% ethanol, and dissolved in RNase-free water.

[Synthesis of cDNA from Total RNA]

cDNA was synthesized from the collected total RNA. The cDNA synthesis was carried out using a PrimeScript II 1st strand cDNA synthesis kit (Takara) in accordance with the manual.

[Acquisition of REF Gene from cDNA]

REF gene was obtained using the prepared 1st strand cDNA as a template. PCR was performed using a KOD-plus-Neo (Toyobo Co., Ltd.) in accordance with the manual. The PCR reaction involved 35 cycles with each cycle consisting of 10 seconds at 98° C., 30 seconds at 58° C., and 1 minute at 68° C.

The REF gene was obtained using the following primers:

```
Primer 1:
5'-tttctcgagatggctgaagacgaagac-3',

Primer 2:
5'-tttggatcctcaattctctccataaaac-3'.
```

REF gene was obtained as above. The gene was sequenced to identify the full-length nucleotide sequence and amino acid sequence. The nucleotide sequence of REF is given by SEQ ID NO: 3. The amino acid sequence of REF is given by SEQ ID NO: 4.

[Vector Construction]

The obtained DNA fragment was subjected to dA addition and then inserted into pGEM-T Easy vector using a pGEM-T Easy Vector System (Promega) to prepare pGEM-REF.

[Transformation of *E. coli*]

*E. coli* DH5α was transformed with the prepared vector, the transformant was cultured on LB agar medium containing ampicillin and X-gal, and *E. coli* cells carrying the introduced target gene were selected by blue/white screening.

[Plasmid Extraction]

The *E. coli* cells transformed with the plasmid containing the target gene were cultured overnight at 37° C. on LB liquid medium. After the culture, the cell bodies were collected, and the plasmid was collected. A FastGene Plasmid mini kit (Nippon Genetics Co., Ltd.) was used for plasmid collection.

It was confirmed by sequence analysis that there were no mutations in the nucleotide sequence of the gene inserted into the collected plasmid.

[Preparation of Vector for Cell-Free Protein Synthesis]

The pGEM-REF obtained in the above "Vector construction" was treated with the restriction enzymes Xho I and Bam HI, and inserted into a pEU-E01-MCS-TEV-His-C1 cell-free expression vector that had been treated similarly with Xho I and Bam HI, to prepare pEU-C1-REF.

[Transformation of *E. coli*]

*E. coli* DH5α was transformed with the prepared vector, the transformant was cultured on LB agar medium containing ampicillin and X-gal, and *E. coli* cells carrying the introduced target gene were selected by colony PCR.

[Plasmid Extraction]

The *E. coli* cells transformed with the plasmid containing the target gene were cultured overnight at 37° C. on LB liquid medium. After the culture, the cell bodies were collected, and the plasmid was collected. A FastGene Plasmid mini kit (Nippon Genetics Co., Ltd.) was used for plasmid collection.

[Preparation of Rubber Particles]

Rubber particles were prepared from *Hevea* latex by five stages of centrifugation. To 900 mL of *Hevea* latex was added 100 mL of 1 M Tris buffer (pH 7.5) containing 20 mM dithiothreitol (DTT) to prepare a latex solution. The latex solution was centrifuged in stages at the following different speeds: 1000×g, 2000×g, 8000×g, 20000×g, and 50000×g. Each stage of centrifugation was carried out for 45 minutes at 4° C. To the rubber particle layer remaining after the centrifugation at 50000×g was added 3-[(3-cholamidopropyl)dimethylamino]-propanesulfonate (CHAPS) at a final concentration of 0.1 to 2.0×CMC (0.1 to 2.0 times the critical micelle concentration CMC) to wash the rubber particles. After the washing, the rubber particles were collected by ultracentrifugation (40000×g, 4° C., 45 minutes), and re-suspended in an equal amount of 100 M Tris buffer (pH 7.5) containing 2 mM dithiothreitol (DTT).

[Cell-Free Protein Synthesis Reaction (Step 1: mRNA Transcription Reaction)]

Cell-free protein synthesis was performed using a WEPRO7240H expression kit (CellFree Sciences Co., Ltd.). An mRNA transcription reaction was performed using the pEU-C1-REF obtained in the above "Preparation of vector for cell-free protein synthesis" as a template in accordance with the protocol of the WEPRO7240H expression kit.

[Purification of mRNA]

After the transcription reaction, the resulting mRNA was purified by ethanol precipitation.

[Cell-Free Protein Synthesis Reaction (Step 2: Protein Synthesis by Dialysis)]

The following amounts were added to a dialysis cup (MWCO 12000, Bio-Teck). A total amount of 60 μL of a reaction solution was prepared according to the protocol of the WEPRO7240H expression kit. To the reaction solution was added 1 to 2 mg of the rubber particles. Separately, 650 μL of SUB-AMIX was added to a No. 2 PP container (Maruemu container).

The dialysis cup was set in the No. 2 PP container, and a protein synthesis reaction was initiated at 26° C. The addition of mRNA and the replacement of the outer dialysis solution (SUB-AMIX) were performed twice after the initiation of the reaction.

Figure 1:
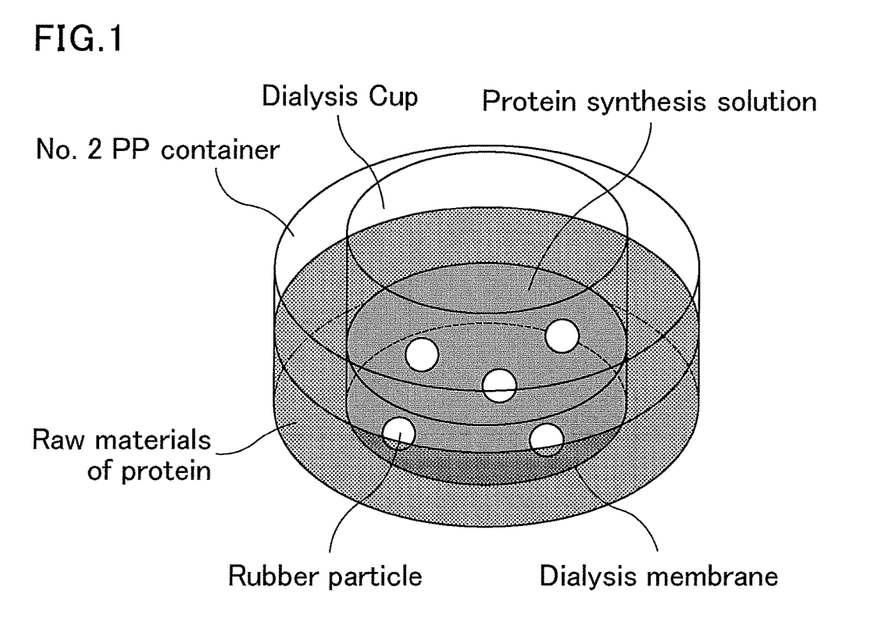
FIG. 1 is a schematic diagram illustrating the dialysis process in the examples.

The reaction was carried out for 24 hours. A schematic diagram illustrating the dialysis process is shown in FIG. 1.

[Collection of Rubber Particles after Reaction]

The solution in the dialysis cup was transferred to a new 1.5 µL tube, and the reacted rubber particles were collected by ultracentrifugation (40000×g, 4° C., 45 minutes) and re-suspended in an equal amount of 100 M Tris buffer (pH 7.5) containing 2 mM dithiothreitol (DTT).

[Measurement of Particle Size of Reacted Rubber Particles]

The particle size of the rubber particles collected after the reaction was measured using a zeta-potential & particle size analyzer ELSZ available from Photal (Otsuka Electronics Co., Ltd).

Comparative Example 1

Preparation of Rubber Particles

Rubber particles were prepared as in Example 1.

[Cell-Free Protein Synthesis Reaction (Step 1: mRNA Transcription Reaction)]

Cell-free protein synthesis was performed using a WEPRO7240H expression kit (CellFree Sciences Co., Ltd.). An mRNA transcription reaction was performed using the cell-free expression vector pEU-E01-His-TEV-MCS-N2 as a template in accordance with the protocol of the WEPRO7240H expression kit.

[Purification of mRNA]

After the transcription reaction, the resulting mRNA was purified by ethanol precipitation.

[Cell-Free Protein Synthesis Reaction (Step 2: Protein Synthesis by Dialysis)]

The protein synthesis reaction was carried out as in Example 1 except for using the above mRNA.

[Collection of Rubber Particles after Reaction]

The reacted rubber particles were collected as in Example 1, and re-suspended in an equal amount of 100 M Tris buffer (pH 7.5) containing 2 mM dithiothreitol (DTT).

[Measurement of Particle Size of Reacted Rubber Particles]

The particle size of the rubber particles collected after the reaction was measured as in Example 1.

Comparative Example 2

Extraction of Total RNA from *Hevea* Latex

The extraction was carried out in Example 1.

[Synthesis of cDNA from Total RNA]

The synthesis was carried out as in Example 1.

[Acquisition of NgBR Gene from cDNA]

NgBR gene was obtained using the prepared 1st strand cDNA as a template. PCR was performed using a KOD-plus-Neo (Toyobo Co., Ltd.) in accordance with the manual. The PCR reaction involved 35 cycles with each cycle consisting of 10 seconds at 98° C., 30 seconds at 58° C., and 1 minute at 68° C.

The NgBR gene was obtained using the following primers:

```
Primer 3:
5'-tttctcgagatggatttgaaacctggagctg-3',

Primer 4:
5'-tttctcgagtcatgtaccataattttgctgcac-3'.
```

NgBR gene (HRTBP) was obtained as above. The gene was sequenced to identify the full-length nucleotide sequence and amino acid sequence. The nucleotide sequence of HRTBP is given by SEQ ID NO: 7. The amino acid sequence of HRTBP is given by SEQ ID NO: 8.

[Vector Construction]

The obtained DNA fragment was subjected to dA addition and then inserted into pGEM-T Easy vector using a pGEM-T Easy Vector System (Promega) to prepare pGEM-HRTBP.

[Transformation of *E. coli*]

The transformation was carried out as in Example 1 but using the prepared vector.

[Plasmid Extraction]

The plasmid extraction was carried out as in Example 1.

[Preparation of Vector for Cell-Free Protein Synthesis]

The pGEM-HRTBP obtained in the above "Vector construction" was treated with the restriction enzyme Xho I, and inserted into a pEU-E01-MCS-TEV-His-C1 cell-free expression vector that had been treated similarly with Xho I, to prepare pEU-C1-HRTBP.

[Transformation of *E. coli*]

The transformation was carried out as in Example 1 but using the prepared vector.

[Plasmid Extraction]

The plasmid extraction was carried out as in Example 1.

[Preparation of Rubber Particles]

Rubber particles were prepared as in Example 1.

[Cell-Free Protein Synthesis Reaction (Step 1: mRNA transcription reaction)]

Cell-free protein synthesis was performed using a WEPRO7240H expression kit (CellFree Sciences Co., Ltd.). An mRNA transcription reaction was performed using the pEU-C1-HRTBP obtained in the above "Preparation of vector for cell-free protein synthesis" as a template in accordance with the protocol of the WEPRO7240H expression kit.

[Purification of mRNA]

After the transcription reaction, the resulting mRNA was purified by ethanol precipitation.

[Cell-Free Protein Synthesis Reaction (Step 2: Protein Synthesis by Dialysis)]

The protein synthesis reaction was carried out as in Example 1 except for using the above mRNA.

[Collection of Rubber Particles after Reaction]

The reacted rubber particles were collected as in Example 1, and re-suspended in an equal amount of 100 M Tris buffer (pH 7.5) containing 2 mM dithiothreitol (DTT).

[Measurement of Particle Size of Reacted Rubber Particles]

The particle size of the rubber particles collected after the reaction was measured as in Example 1.

Example 2

Extraction of Total RNA from *Hevea* Latex

The extraction was carried out as in Example 1.

[Synthesis of cDNA from Total RNA]

The synthesis was carried out as in Example 1.

[Acquisition of SRPP Gene from cDNA]

SRPP gene was obtained using the prepared 1st strand cDNA as a template. PCR was performed using a KOD-plus-Neo (Toyobo Co., Ltd.) in accordance with the manual.

The PCR reaction involved 35 cycles with each cycle consisting of 10 seconds at 98° C., 30 seconds at 58° C., and 1 minute at 68° C.

The SRPP gene was obtained using the following primers:

```
Primer 5:
5'-tttctcgagatggctgaagaggtggag-3',

Primer 6:
5'-tttggatccttatgatgcctcatctcc-3'.
```

SRPP gene was obtained as above. The gene was sequenced to identify the full-length nucleotide sequence and amino acid sequence. The nucleotide sequence of SRPP is given by SEQ ID NO: 11. The amino acid sequence of SRPP is given by SEQ ID NO: 12.

[Vector Construction]

The obtained DNA fragment was subjected to dA addition and then inserted into pGEM-T Easy vector using a pGEM-T Easy Vector System (Promega) to prepare pGEM-SRPP.

[Transformation of *E. coli*]

The transformation was carried out as in Example 1 but using the prepared vector.

[Plasmid Extraction]

The plasmid extraction was carried out as in Example 1.

[Preparation of Vector for Cell-Free Protein Synthesis]

The pGEM-SRPP obtained in the above "Vector construction" was treated with the restriction enzyme Xho I and Bam HI, and inserted into a pEU-E01-MCS-TEV-His-C1 cell-free expression vector that had been treated similarly with Xho I and Bam HI, to prepare pEU-C1-SRPP.

[Transformation of *E. coli*]

The transformation was carried out as in Example 1 but using the prepared vector.

[Plasmid Extraction]

The plasmid extraction was carried out as in Example 1.

[Preparation of Rubber Particles]

Rubber particles were prepared as in Example 1.

[Cell-Free Protein Synthesis Reaction (Step 1: mRNA Transcription Reaction)]

Cell-free protein synthesis was performed using a WEPRO7240H expression kit (CellFree Sciences Co., Ltd.). An mRNA transcription reaction was performed using the pEU-C1-SRPP obtained in the above "Preparation of vector for cell-free protein synthesis" as a template in accordance with the protocol of the WEPRO7240H expression kit.

[Purification of mRNA]

After the transcription reaction, the resulting mRNA was purified by ethanol precipitation.

[Cell-Free Protein Synthesis Reaction (Step 2: Protein Synthesis by Dialysis)]

The protein synthesis reaction was carried out as in Example 1 except for using the above mRNA.

[Collection of Rubber Particles after Reaction]

The reacted rubber particles were collected as in Example 1, and re-suspended in an equal amount of 100 M Tris buffer (pH 7.5) containing 2 mM dithiothreitol (DTT).

[Measurement of Particle Size of Reacted Rubber Particles]

The particle size of the rubber particles collected after the reaction was measured as in Example 1.

Table 1 shows the results of the measurement of the particle size of the reacted rubber particles in Examples 1 and 2 and Comparative Examples 1 and 2.

TABLE 1

|  | Example 1 | Example 2 | Comparative Example 1 | Comparative Example 2 |
|---|---|---|---|---|
| Bound protein | REF | SRPP | None | HRTBP |
| Average rubber particle size (nm) | 485 | 505 | 941 | 1633 |

The results in Table 1 show that when rubber particles were bound to REF or SRPP which are REF family proteins, the resulting rubber particles maintained the small average particle size. This demonstrated that by binding a REF family protein to rubber particles, the rubber particles are stabilized and exhibit a reduced coagulation tendency even at temperatures that are not low, e.g. at room temperature, and therefore rubber particles with a reduced coagulation tendency are produced.

SEQUENCE LISTING FREE TEXT

SEQ ID NO: 1: Primer 1
SEQ ID NO: 2: Primer 2
SEQ ID NO: 3: Nucleotide sequence of gene coding for REF derived from *Hevea brasiliensis*
SEQ ID NO: 4: Amino acid sequence of REF derived from *Hevea brasiliensis*
SEQ ID NO: 5: Primer 3
SEQ ID NO: 6: Primer 4
SEQ ID NO: 7: Nucleotide sequence of gene coding for HRTBP derived from *Hevea brasiliensis*
SEQ ID NO: 8: Amino acid sequence of HRTBP derived from *Hevea brasiliensis*
SEQ ID NO: 9: Primer 5
SEQ ID NO: 10: Primer 6
SEQ ID NO: 11: Nucleotide sequence of gene coding for SRPP derived from *Hevea brasiliensis*
SEQ ID NO: 12: Amino acid sequence of SRPP derived from *Hevea brasiliensis*

The invention claimed is:

1. A method for producing rubber particles with a reduced coagulation tendency, the method comprising
a step of performing protein synthesis in the presence of both rubber particles and a cell-free protein synthesis solution containing an mRNA coding for a rubber elongation factor (REF) family protein to bind the REF family protein to the rubber particles.

2. The method for producing rubber particles with a reduced coagulation tendency according to claim 1, wherein the REF family protein is derived from *Hevea brasiliensis*.

3. The method for producing rubber particles with a reduced coagulation tendency according to claim 1, wherein the cell-free protein synthesis solution contains a germ extract.

4. The method for producing rubber particles with a reduced coagulation tendency according to claim 3, wherein the germ extract is derived from wheat.

5. The method for producing rubber particles with a reduced coagulation tendency according to claim 1, wherein the rubber particles are present in the cell-free protein synthesis solution at a concentration of 5 to 50 g/L.

6. A method for producing a pneumatic tire, the method comprising the steps of:
synthesizing rubber from the rubber particles obtained by the method according to claim 1;
kneading the rubber with an additive to obtain a kneaded mixture;
building a green tire from the kneaded mixture; and
vulcanizing the green tire.

7. A method for producing a rubber product, the method comprising the steps of:
synthesizing rubber from the rubber particles obtained by the method according to claim 1;
kneading the rubber with an additive to obtain a kneaded mixture;
forming a raw rubber product from the kneaded mixture; and
vulcanizing the raw rubber product.

* * * * *

UNITED STATES PATENT AND TRADEMARK OFFICE
CERTIFICATE OF CORRECTION

PATENT NO. : 10,059,780 B2
APPLICATION NO. : 15/170278
DATED : August 28, 2018
INVENTOR(S) : Haruhiko Yamaguchi et al.

It is certified that error appears in the above-identified patent and that said Letters Patent is hereby corrected as shown below:

On the Title Page

Item (73), change:
"SUMITOMO RUBBER INDUSTRIES, LTD., Kobe-shi (JP)"
To:
-- SUMITOMO RUBBER INDUSTRIES, LTD., Kobe-shi (JP) and
TOHOKU UNIVERSITY, Sendai-shi (JP) --

Signed and Sealed this
Sixth Day of August, 2019

Andrei Iancu
*Director of the United States Patent and Trademark Office*